United States Patent [19]

Taylor

[11] 4,033,721

[45] July 5, 1977

[54] ANALYSIS OF GENTIAN VIOLET RESIDUE IN TISSUE

[75] Inventor: Gregg W. Taylor, Murrayville, Ga.

[73] Assignee: A.H.P., Inc., Gainesville, Ga.

[22] Filed: Aug. 16, 1976

[21] Appl. No.: 714,895

Related U.S. Application Data

[63] Continuation-in-part of Ser. No. 342,290, March 16, 1973, Pat. No. 3,916,027, Continuation-in-part of Ser. No. 454,000, March 22, 1974, Pat. No. 3,915,637, Continuation-in-part of Ser. No. 595,876, July 14, 1975, Continuation-in-part of Ser. No. 625,873, Oct. 24, 1975, Continuation-in-part of Ser. No. 658,760, Feb. 17, 1976, Pat. No. 3,975,158.

[52] U.S. Cl. .......................... 23/230 B; 23/230 R; 424/329

[51] Int. Cl.² ........................................ G01N 33/16
[58] Field of Search ................... 23/230 B, 230 R; 424/141, 329

[56] References Cited

UNITED STATES PATENTS

| | | | |
|---|---|---|---|
| 3,915,637 | 10/1975 | Taylor | 23/230 B |
| 3,916,027 | 10/1975 | Taylor | 424/329 |
| 3,975,158 | 8/1976 | Taylor | 23/230 B |

*Primary Examiner*—Robert M. Reese
*Attorney, Agent, or Firm*—Fisher, Christen & Sabol

[57] ABSTRACT

A process for the analysis of gentian violet in animal or poultry tissue, animal or poultry manure, animal or poultry feed, or eggs. The gentian violet is quantitatively determined.

24 Claims, No Drawings

ANALYSIS OF GENTIAN VIOLET RESIDUE IN TISSUE

This is a continuation-in-part of applicant's U.S. Ser. No. 342,290, filed on Mar. 16, 1973, now U.S. Pat. No. 3,916,027, of applicant's U.S. Ser. No. 454,000, filed on Mar. 22, 1974 now U.S. Pat. No. 3,915,637, of applicant's copending U.S. Ser. No. 595,876, filed on July 14, 1975, of applicant's copending U.S. Ser. No. 625,873, filed on Oct. 24, 1975, and applicant's copending U.S. Ser. No. 658,760, filed on Feb. 17, 1976 now U.S. Pat. No. 3,975,158.

BACKGROUND OF THIS INVENTION

1. Field of This Invention

This invention relates to processes for the analysis of residual gentian violet in tissue, eggs, manure or feed.

2. Prior Art

U.S. Pat. No. 3,915,637 involves a process for the analysis of the residual gentian violet in feed, tissue, eggs or manure. The process includes extracting substantially all of the fat in the feed, tissue, eggs or manure using a fat solvent. (The extraction is preferably done at room temperature. The fat solvent is separated from the feed, tissue, eggs or manure, preferably, by means of centrifuging.) The fat-extracted feed or manure is dried. A known amount of acidified ethanol is admixed with the fat-extracted feed, eggs, tissue or manure, and the resultant admixture is left standing (preferably for 48 hours). The acidified alcohol is separated from the resultant admixture. The amount of gentian violet in the acidified alcohol is determined by spectrophotometrical comparison with acidified alcohol standards containing set amounts of gentian violet.

The extraction, separation and determination steps are repeated until no gentian violet is found to be present in the acidified alcohol, the total of the gentian violet found from the determination steps being the total amount of gentian violet present in the feed, eggs, tissue or manure.

Preferably the fat extraction step involves first extracting the fat from the manure, tissue, eggs or feed at least once with hexane. The preferred fat solvent is petroleum ether, when a one-step extraction process is used, and is the use of petroleum ether, in the first step and the use of hexane in the second step, when a two-step extraction step is used. Other fat solvents can be used. Preferably the acidified alcohol contains 1 ml. of concentrated HCl per 100 ml. of ethanol. Other acids such as concentrated sulfuric acid and concentrated nitric acid can be used in place of the concentrated HCl. Other suitable solvents can be used in place of the acidified alcohol. The determinations can be made by any conventional method, but preferably are made using a spectrophotometer, such as, a Turner spectrophotometer.

The patent also involves a process for checking the accuracy of a process for the analysis of residual gentian violet in feed or manure of animal or poultry.

BROAD DESCRIPTION OF THIS INVENTION

An object of this invention is to provide a more sensitive and simplified analytic process for quantitatively determining the gentian violet content of materials, such as, animal or poultry tissure. A further object of this invention is to provide a process for checking the accuracy of such analytic process. Other objects and advantages of this process are set out herein or obvious herefrom to one ordinarily skilled in the art.

the process of this invention achieves the objects and advantages of this invention.

This invention involves a process for the analysis of gentian violet in a material. The process includes finely particulating a known amount of material containing gentian violet, unless such material is already in a finely divided state. A known amount of acidified ethanol is admixed with the finely particulated tissue and the resultant admixture is allowed to stand. The acidified ethanol removes the gentian violet from the material. The acidified ethanol is separated from the admixture by centrifugation. Any spectrophotometrical interfering substance is removed from the acidified ethanol by passing the acidified ethanol through a chromatograph column. The amount of gentian violet in the acidified ethanol and the background measurement of the acidified ethanol is determined by spectrophotometrical means. The gentian violet in said acidified ethanol is quenched by adding to the acidified ethanol a chemical substance which selectively renders the gentian violet non-detectable by spectrophotometric means without disturbing the spectrophotometric background of the acidified ethanol. The background measurement of the acidified ethanol is determined by spectrophotometrical means. The quantitative amount of gentian violet in the material is calculated using the two spectrophotometrical measurements.

Preferably the material containing gentian violet is animal tissure, poultry tissue, eggs, animal feed, poultry feed, animal manure or poultry manure. Preferably the acidified ethanol is acidified by HCl. Preferably the two spectrophotometric measurements are made at 590 m$\mu$.

This invention also includes an improvement in such process for the analysis of gentian violet in a material. The improved process has a sensitivity of as little as four or five parts per billion of gentian violet. The improved process for the analysis of gentian violet in a material includes finely particulating a known amount of material containing gentian violet, unless such material is already in a finely divided state. A known amount of acidified ethanol is admixed with the finely particulated material and the resultant admixture is allowed to stand—the acidifiedethanol removing the gentian violet from the material. The acidified ethanol is separated from the admixture by centrifugation. any spectrophotometrical interfering substance is removed from the acidified ethanol by passing the acidified ethanol through a chromatograph column containing a basic sorbent, the acid in the acidified ethanol (c) being neutralized by the basic sorbent. The amount of gentian violet in the neutralized ethanol and the background measurement of the nautralized ethanol is determined by spectrophotometrical means. The gentian violet in the neutralized ethanol is determined by spectrophotometrical means. The gentian violet in the neutralized ethanol is quenched by adding to the neutralized ethanol a chemical substance which selectivity renders the gentian violet non-detectable by spectrophotometric means without disturbing the spectrophotometric background of the neutralized ethanol. The background measurement of the neutralized ethanol is determined by spectrophotometrical means. The quantitative amount of gentian violet in said material is calculated using the spectrophotometrical measurements of the above steps.

The basic sorbent is most preferably Alumin-AR. Preferably the material containing gentian violet is animal tissure, poultry tissue, eggs, animal feed, poultry feed, animal manure or poultry manure. Preferably the acidified ethanol was acidified by H. Preferably the two spectrophotometric measurements are made at 590 m$\mu$.

This invention also includes a further improvement in such process for the analysis of gentian violet in a material. The further improved process has a sensitivity of as little as one or two parts per billion of gentian violet in such material. The further improved process for the analysis of gentian violet in a material includes a step inserted between two steps in the improved process of this process. After any spectrophotometrical interfering substance is removed from the acidified ethanol by passing the acidified ethanol through a chromatograph column containing a basic sorbent (the acid in the acidified ethanol (c) being neutralized by the basic sorbent), and before the amount of gentian violet in the neutralized ethanol and the background measurement of the neutralized ethanol is determined by spectrophotometrical means, the neutralized ethanol is concentrated so that the concentration of the gentian violet therein is increased.

Preferably the basic sorbent is Alumin-AR. Also, preferably the neutralized ethanol is concentrated by a factor of at least tenfold. Preferably the material containing gentian violet is animal tissue, poultry tissue, eggs, animal feed, poultry feed, animal manure or poultry manure. Preferably the acidified ethanol was acidified by H. Preferably the two spectrophotometric measurements are made at 590 m$\mu$.

This invention also includes a process for checking the accuracy of the process for the analysis of gentian violet in a material. The checking process involves finely particulating a known amount of a material known not to contain any gentian violet, unless such material is already in a finely divided state. A known amount of at least one aqueous solution containing a known amount of gentian violet is added to a known amount of the material known not to contain any gentian violet to form at least one spiked sample. A known amount of acidified ethanol is admixed with the finely particulated tissue and the resultant admixture is let stand. The acidified ethanol removes the gentian violet from the material. The acidified ethanol is separated from the admixture by centrifugation. Any spectrophotometrical interfering substance is removed from the acidified ethanol by passing the acidified ethanol through a chromatograph column. The amount of gentian violet in the acidified ethanol and the background measurement of the acidified ethanol is determined by spectrophotometrical means. The gentian violet in the acidified ethanol is quenched by adding to the acidified ethanol a chemical substance which selectively renders the gentian violet non-detectable by spectrophotometric means without disturbing the spectrophotometric background of the acidified ethanol. The background measurement of the acidified ethanol is determined by spectrophotometrical means. The quantitative amount of gentian violet in the spiked material is calculated using the two spectrophotometrical measurements. The amount of gentian violet in the spiked samples gives the accuracy of the procedure for the analysis of gentian violet in the spiked material by direct comparison with the known amount of gentian violet placed in the spiked sample.

Preferably at least two spiked samples are prepared, each of the spiked samples having a different amount of gentian violet. Preferably the material containing gentian violet is animal tissue, poultry tissue, eggs, animal feed, poultry feed, animal manure or poultry manure. Preferably the acidified ethanol was acidified by HCl. Preferably the two spectrophotometric measurements are made at 590 m$\mu$.

This invention further includes a process for checking the accuracy of the improved process of this invention for the analysis of gentian violet. The process for checking the accuracy of the improved process for the analysis of gentian violet in a material includes finely particulating a known amount of a material known not to contain any gentian violet, unless such material is already in a finely divided state. A known amount of at least one aqueous solution containing a known amount of gentian violet is added to a known amount of the material known not to contain any gentian violet to form at least one spiked sample. A known amount of acidified ethanol is admixed with the spiked sample and the resultant admixture is let stand, the acidified ethanol removing the gentian violet from the material. The acidified ethanol is separated from the admixture by centrifugation. Any spectrophotometrical interfering substance is removed from the acidified ethanol by passing the acidified ethanol through a chromatograph column containing a basic sorbent, the acid in the acidified ethanol being neutralized. The amount of gentian violet in the neutralized ethanol and the background measurement of said neutralized ethanol is determined by spectrophotometrical means. The gentian violet in the neutralized ethanol is quenched by adding to the neutralized ethanol a chemical substance which selectively renders the gentian violet non-detectable by spectrophotometric means without disturbing the spectrophotometric background of the acidified ethanol. The background measurement of the neutralized ethanol is determined by spectrophotometrical means. The quantitative amount of gentian violet in the spiked material is calculated using the spectrophotometrical measurements of the above steps. The amount of gentian violet for the spiked samples gives the accuracy of the procedure for the analysis of gentian violet in the spiked material by direct comparison with the known amount of gentian violet placed in the spiked sample.

Preferably the basic sorbent is Alumin-AR. Preferably the neutralized ethanol is concentrated by a factor of at least tenfold. Also, preferably the material containing gentian violet is animal tissue, poultry tissue, eggs, animal feed, poultry feed, animal manure or poultry manure. Preferably the acidified ethanol was acidified by HCl. Preferably the two spectrophotometric measurements are made at 590 m$\mu$.

This invention further includes a process for checking the accuracy of the further improved process of this invention for the analysis of gentian violet. The process for checking the accuracy of the further improved process for the analysis of gentian violet in a material includes finely particulating a known amount of a material known not to contain any gentian violet, unless such material is already in a finely divided state. A known amount of at least one aqueous solution containing a known amount of gentian violet is added to a known amount of the material known not to contain any gentian violet to form at least one spiked sample. A known amount of acidified ethanol is admixed with the spiked sample and the resultant admixture is let stand, the acidified ethanol removing the gentian violet from the material. The acidified ethanol is separated from the admixture by centrifugation. Any spectrophotometrical interfering substance is removed from the acidified ethanol by passing the acidified ethanol through a chromatograph column containing a basic sorbent, the acid in the acidified ethanol being neutralized. The neutralized ethanol is concentrated so that the concentration of the gentian violet is increased. The amount of gentian violet in the neutralized ethanol and the background measurement of said neutralized ethanol is determined by spectrophotometrical means. The gentian violet in the neutralized ethanol is quenched by adding to the neutralized ethanol a chemical substance which selectively renders the gentian violet non-detectable by spectrophotometric means without disturbing the spectrophotometric background of the acidified ethanol. The background measurement of the neutralized ethanol is determined by spectrophotometrical means. The quantitative amount of gentian violet in the spiked material is calculated using the spectrophotometrical measurements of the above steps. The amount of gentian violet for the spiked samples gives the accuracy of the procedure for the analysis of gentian violet in the spiked material by direct comparison with the known amount of gentian violet placed in the spiked sample.

Preferably the basic sorbent is Alumin-AR. Preferably the neutralized ethanol is concentrated by a factor of at least tenfold. Also, preferably the material containing gentian violet is animal tissue, poultry tissue, eggs, animal feed, poultry feed, animal manure or poultry manure. Preferably the acidified ethanol was acidified by HCl. Preferably the two spectrophotometric measurements are made at 590 m$\mu$.

An advantage of this invention over the prior art is that the process of this invention is much more accurate and sensitive than the prior method or methods. The best prior art method is that of U.S. Pat. No. 3,915,637.

This invention achieves far more accuracy and sensitivity than the process of U.S. Pat. No. 3,915,637 by the use of at least two improvements. The first improvement involves the passage of the initial extraction solution through a chromatographic column to trap all of the interfering materials to provide a clear eluant for spectrophotometric analysis. The second improvement involves quenching the gentian violet in the eluant to allow for quantitative calculation of the gentian violet recovery. This quenching technique eliminates the question of background interferences as only the gentian violet is quenched from the eluant.

The sensitivity of the process of this invention, due mostly to the two above-described process improvements, is greatly improved over that of the process of U.S. Pat. No. 3,915,637 with a Turner spectrophotometer, or its equivalent, utilizing 13 mm cuvettes, the analytical process of U.S. Pat. No. 3,915,637 has a sensitivity at most of 0.1 ppm gentian violet, whereas the analytical process of this invention has a sensitivity of 0.1 to 0.04 ppm gentian violet. With a Backman D.U. spectrophotometer, or its equivalent, utilizing 100 mm cells, the analytical process of U.S. Pat. No. 3,915,637 has a sensitivity at most of 0.01 ppm gentian violet, whereas the analytical process of this invention has a sensitivity of 0.01 to 0.005 ppm gentian violet. So the analytical process of this invention is eminently applicable to the quantitative determination of the gentian violet content of or residue in tissue samples containing 0.1 ppm or less gentian violet (depending on the spectrophotometer and cells utilized in the determination). This is also so with eggs and manure.

The improved process of this invention achieves an increased of sensitivity to a 5 ppb level.

The process of this invention does not require an involved fat extraction step (using fat solvents, e.g., petroleum ether and hexane in sequence, followed by a separation of the fat solvent). This invention uses the much more accurate chromatograph column to remove the spectrophotometric interfering substances after the acid-ethanol extraction step.

An advantage of this invention is that no process is necesary for checking the accuracy of the analytical process of this invention. Such a checking can be used if desired, but is not necessary due to the inherent accuracy of the invention process.

An advantage of the further improved process of this invention is that it has a sensitivity as low as 1 or 2 ppb—the improved process of this invention has a lower sensitivity of at most 5 ppb. In the present state of quantitative analysis, this is an outstanding increase in sensitivity.

DETAILED DESCRIPTION OF THIS INVENTION

This invention can even be used to detect gentian violet residues in tissue. In such the gentian violet has reacted with the tissue. Spiked tissues may not achieve this chemical bonding.

As used herein, the term "poultry" means domestic fowl including chickens, ducks, turkeys, geese, etc. As used herein, the term "animal" includes domestic pigs, other swine, cattle, sheep, goats, rabbits, etc. The term "animal" includes humans and non-human animals.

As used herein, the term "gentian violet" is hexamethylpararosaniline chloride or a mixture of at least 90 percent of hexamethylpararosaniline chloride with minor portions of pentamethylpararosaniline chloride and/or tetramethylpararosaniline chloride, and preferably meeting all specifications of quality for U.S.P. grade as listed in the United States Pharmacopiea XIV. This assures that none of the deadly heavy metals is left as a residue in animal or poultry tissue that is to be consumed by man.

Gentian violet is a dark green powder or greenish, glistening pieces with a metallic luster. Gentian violet is soluble in water, chloroform and ehtanol. Other names for gentian violet are methyl rosaniline chloride and crystal violet.

Gentian violet, both as a contaminant in water and as a residue in poultry manure, is biodegradable in the presence of the ultra-violet rays of sunlight.

Another name for Candida albicans is Monilia albicans. Candida albicans, a yeast-like organism, is the usual cause of moniliasis pneumonia, meningitis and other forms of moniliasis. It is normally saprophytic but may be come pathogenic after the administration of certain antibiotics. (Antibiotics are often used in relatively large amounts in animal and poultry feeds. The use of the antibiotics allows molds and fungi to grow.) The use of gentian violet in water and feed is useful in eliminating and preventing internal infestation of Candida albicans, for example, in the intestines, and infestation of Candida albicans in drinking water.

Gentian violet inhibits the growth of and destroys Candida albicans without materially reducing the growth of and activity of the normal coliform bacteria present in the intestinal tract, which is necessary in synthesizing important nutritional factors.

U.S. Pat. Nos. 3,916,027 and 3,915,637 disclose the use of gentian violet as an additive to animal and poultry feed for the prevention and treatment of candidiasis caused by Candida albicans. As a result there is a buildup of gentian violet residue in the tissue of any animals and poultry consuming feed containing gentian violet. The residue levels involved in consumption at the levels given in U.S. Pat. No. 3,916,027 are not toxic or harmful to the consuming animal or poultry. The consuming animals or poultry are put on a withdrawal feed period (i.e., feed which does not contain any gentian violet) to lower the gentian violet residue level when the animals are to be consumed by man. It is important to get as low a gentian violet level as possible in the animal or poultry tissue—the continued consumption of a low (even very low) amount of a chemical may sensitize a human to the chemical. This means the subsequent use of gentian violet as a medicine or medicament for humans who had been so sensitized could be quite harmful to such humans from severe adverse reactions. In view of this it is important to have an analytic procedure to detect much less than 0.1 ppm gentian violet residue (maximum level allowed by the F.D.A.) in animal or poultry tissue that is to be consumed by man. Lower levels are required by the F.D.A. in eggs, so the accuracy of this procedure is also needed in the egg field. The manure field is necessary, among other reasons, to get a complete accounting of the gentian violet consumed by animals or poultry.

The gentian violet is preferably used in the form of a premix concentrate, which can be added to the complete feed as needed. The most preferred premix concentrate contains corn cob fractions, white mineral oil, diatomaceous silica (e.g., Micro-Cel E), distilled water and 1.55 percent of gentian violet.

The concentration of gentian violet in the premix concentrate can easily be as high as 60 percent; it is preferably between 0.1 and 10 percent and is most preferably 1.55 percent. A useful gentian violet premix concentrate is premix ViGen (concentrate) obtainable from A.H.P., Inc., Gainesville, Georgia.

The premix concentrate can contain any material that is used in a complete poultry feed or animal feed. The premix concentrate can be used in the form of a liquid or solid admixture. The liquid is best in the form of a very viscous suspension or similar semi-fluid. Preferably a solid premix concentrate is used even though it may contain a liquid material such as white mineral oil which reduces the dust factor in the premix.

The premix concentrate is used for treatment of Candida albicans by adding it to the complete poultry or animal feed for a period of about seven days, although the time can be more or less as needed. When the premix concentrate contains 1.55 percent of gentian violet, preferably two pounds of the premix is used per ton of complete poultry or animal feed. That reflects a preferred concentration of about 0.00155 percent of gentian violet in the complete poultry feed. Effective concentrations of gentian violet are quite wide, but an example of the range is 0.0001 to 0.01 percent of gentian violet per ton of complete poultry or animal feed.

The above treatment times and concentrations in the complete poultry or animal feed apply even when the gentian violet is directly admixed with the complete poultry or animal feed without going through the intermediate premix concentrate form.

The premix is used for prevention of Candida albicans by adding it to the complete poultry or animal feed on a continuous basis. (After treatment with the premix, it should be used on a continuous basis to achieve prevention.) When the premix contains 1.55 percent of gentian violet, preferably one pound of the premix is used per ton of complete poultry or animal feed. That reflects a preferred concentration of about 0.00077 percent of gentian violet in the complete poultry or animal feed. Effective concentrations of gentian violet are quite wide, but an example of the range is 0.00005 to 0.005 percent of gentian violet per ton of complete poultry or animal feed.

The above treatment times and concentrations in the complete poultry or animal feed apply even when the gentian violet is directly admixed with the complete poultry or animal feed without going through the intermediate premix concentrate form.

Any complete poultry feed or basal poultry feed can be used. It can contain, for example, ground yellow corn, soybean oil meal, steamed bone meal, ground limestone, iodized salt, manganese sulfate, Vitamin A oil, dry Vitamin D-3, riboflavin, Vitamin B-12 and niacin. It can also contain, for example, fish meal and meat meal.

Any complete animal feed or basal animal feed can be used; it can contain, for example, any of the following ingredients: mogul starch, iodized salt, dry Vitamin D-3, riboflavin, Vitamin B-12, niacin, meat meal, calcium pantothenate, cracked or milled grains such as corn, wheat, oats, barley and the like, dried molasses, dried sorghum, soybean meal, cottonseed meal, peanut mean, fish meal, essential amino acids such as lysine, peptides and polypeptides containing essential amino acids, casein, soya bean protein, vitamins such as Vitamins A, E and K, mineral nutrients such as sodium chloride, ferrous salts, magnesium sulfate and calcium salts, proteins, buffers, dextrose, sucrose, lactose, maltose, corn syrup solids, hydrolyzed cereal solids, hay, etc.

An exemplary cattle feed is 73 percent rolled shelled corn, 20 percent ground corn cobs, and a supplement containing soybean meal, alfalfa meal, cane molasses, urea, salt, dicalcium phosphate, vitamin A concentrate and Vitamin D concentrate.

The gentian violet may be consumed as a poultry water sanitizer. It aids in the reduction of Candida albicans contamination in water lines and poultry watering equipment. It may be put directly into poultry water to treat and prevent candidiasis.

The gentian violet is preferably used in the form of a liquid premix concentrate, which can be added to the poultry water on a reqular basis, for example, once a week. It can also be made up into a stock solution and added to the poultry water. The most preferred concentrate contains water and 0.3875 percent of gentian violet, but the concentration usually ranges from 0.05 to 5 percent, although any concentration can be used. The key is to get a sufficiently high concentration in the poultry water itself. The concentration of gentian violet in the poultry water itself should be between 0.001 and 0.05 percent.

The treatment period is preferably one day every week, but can be on any basis as needed to achieve the desired effect.

The gentian violet can be added directly to the poultry water, in which case the above treatment times and concentrations also apply.

The pertinent portions of applicant's copending application Ser. No. 625,693, filed Oct. 24, 1975, entitled "Feed Composition and Process of Sparing Poultry from the Effects of Aflatoxin", is incorporated herein by reference.

U.S. Ser. No. 625,693 discloses a method for sparing an animal or poultry from the toxic effect of a mycotoxin in animal or poultry feed. The method includes feeding a complete feed to the animal or poultry, the complete feed being comprised of (i) gentian violet, and (ii) the remainder inert ingredients. The gentian violet spares the animal or poultry from the effect of mycotoxin in the feed as a contaminant. The gentian violet is present in the feed in an amount between 0.00077 and 0.01 percent by weight, based on the weight of the complete feed.

a premix concentrate can be added to the feed. The premix contains between 0.1 and 10 percent by weight of gentian violet and the remainder inert ingredients. Enough of the premix concentrate to the other ingredients of the feed is used to obtain the recited amount of gentian violet in the feed.

Preferably the feed contains 0.00155 to 0.00232 percent by weight of gentian violet, based on the weight of the complete poultry feed.

Such is quite useful for feeds that are contaminated with as much as 10 p.p.m. or more of mycotoxin.

The sparing effect of gentian violet appears to be a linear function of the concentration of the aflatoxin in the feed.

The growth of the animal or poultry taking mycotoxin-contaminated poultry or animal feed containing gentian violet at the claimed levels is increased at a rate significantly faster than if the animal or poultry had not been fed such mycotoxin-contaminated feed containing gentian violet.

Gentian violet works as a growth promoter when the animal or poultry are even consuming feed which is contaminated with aflatoxin.

The levels of gentian violet used in this invention are low enough not to damage the consuming animal and not to produce an unacceptable residue in food from the animal. The level of residue is extremely low.

Gentian violet is essentially non-absorbable and stable in the pH range of the digestive tract of animals and poultry.

Any complete poultry feed or basal poultry or complete animal feed or basal animal feed can be used.

The greatest mycotoxin effect sparing is achieved in young, maturing animals or poultry, although excellent mycotoxin effect sparing is achieved in grown mature animals or poultry.

An important feature is that there is little or no residue of the gentian violet in the tissue of the animals fed the compositions—this is apparently so due, in part, to the levels of gentian violet used in the compositions of this invention. This means that there is no toxicological danger to animals or humans from ingestion of the edible tissues of animals which have been fed the compositions.

Applicant's claimed concentration ranges in the animal and poultry feeds are important re efficacy, mycotoxin effect sparing in poultry or animals. If amounts lower than applicant's claimed ranges are used, there is little or no efficacy in aflatoxin effect sparing. If an amount of gentian violet is used which is higher than applicant's claimed range (in feed), toxic effects in the poultry can be encountered. The toxic effect can kill the poultry or cause a decrease in the weight gain of the poultry, which represents a serious economic loss to commercial poultry raisers (and loses the advantage of the gentian violet being a growth promoter). The residue build up is a potential health hazard when such higher levels are used.

The pertinent portions of applicant's copending application Ser. No. 625,873, filed Oct. 24, 1975, entitled "Growth Promoter and Process," is incorporated herein by reference. The pertinent portions of applicant's copending U.S. Ser. No. 595,876, filed on July 14, 1975, entitled "Growth Promoter and Process", is incorporated herein by reference.

For the best effects the feed composition of this invention is fed to poultry, hogs or cattle.

Preferably the mix of preparing the feed involves preparing a premix concentrate for addition to the feed which consists only of between 0.1 and 10 percent by weight of gentian violet and the remainder inert ingredients, and then adding enough of the premix concentrate to the other ingredients of feed to obtain the recited amount of gentian violet in the feed. Preferably inert ingredients used in the premix concentrate are diatomaceous silica, corn cob fractions and vegetable oil. Most preferably the feed contains 0.00155 percent by weight of gentian violet, based on the weight of the complete feed.

The gentian violet is preferably used in the form of a premix concentrate, which can be added to the complete feed as needed. The most preferred premix concentrate contains corn cob fractions, white mineral oil, diatomaceous silica (e.g., Micro-Cel E), distilled water and 1.55 percent of gentian violet.

The concentration of gentian violet in the premix concentrate can easily be as high as 60 percent; it is preferably between 0.1 and 10 percent and is most preferably 1.55 percent. A useful gentian violet premix concentrate is premix ViGen (concentrate) obtainable from A.H.P. Inc., Gainesville, Georgia.

The premix concentrate can contain any material that is used in a complete or basal animal or poultry feed. The premix concentrate can be used in the form of a liquid or solid admixture. The liquid is best in the form of a very viscous suspension or similar semi-fluid. Preferably a solid premix concentrate is used even though it may contain a liquid material such as white mineral oil which reduces the dust factor in the premix.

The premix concentrate is used by adding it to the complete poultry feed as long as growth stimulation is wanted. When the premix concentrate contains 1.55 percent of gentian violet, preferably 2 pounds of the premix is used per ton of complete poultry feed for growth stimulation of animals or poultry—this reflects a preferred concentration of about 0.00155 percent of gentian violet in the complete poultry feed. Effective concentrations of gentian violet are within the range of 0.00077 to 0.005 percent of gentian violet per ton of complete poultry feed. The preferred concentrate range of gentian violet is from 0.00085 to 0.01 percent of gentian violet per ton of complete poultry feed. Most preferably female poultry are fed at a gentian violet level of 0.00155 percent per ton of complete poultry feed; and most preferably male poultry are fed at a gentian violet level of 0.00385 percent per ton of complete poultry feed.

The above concentrations in the complete poultry feed apply even when the gentian violet is directly admixed with the complete poultry feed without going through the intermediate premix concentrate form.

The premix is used for growth stimulation by adding it to the complete feed on a continuous basis.

Any complete poultry feed or basal poultry feed or complete animal feed or basal animal feed can be used.

The greatest growth stimulation is achieved in young, maturing animals or poultry, although excellent growth stimulation is achieved in grown mature animals or poultry.

An important feature is that there is little or no residue of the gentian violet in the tissue of the animals fed the compositions —this is apparently so due, in part, to the levels of gentian violet used in the composition. This means that there is no toxicological danger to animals or humans from ingestion of the edible tissues of animals which have been fed the compositions.

Applicant's claimed concentration ranges in the animal and poultry feeds are important re efficacy, growth stimulation and toxicity in poultry or animals. If amounts lower than applicant's claimed ranges are used, there is little or no growth stimulation of animals or poultry. If an amount of gentian violet is used which is higher than applicant's claimed range (in feed), then toxic effects in the poultry can be encountered. The toxic effect can kill the poultry or cause a decrease in the weight gain of the poultry, which represents a serious economic loss to commercial poultry raisers (and loses the advantage of the gentian violet being a growth promoter). The residue build up is a potential health hazard when such higher levels are used.

U.S. Ser. No. 625,873 discloses the use of an effective amount of at least one specific-acting drug along with the gentian violet in the animal or poultry feed.

The eggs, feed, tissue or manure (a known amount) is finely particulated, if necessary. In the case of tissue or eggs, the process preferably includes finely particulating a known amount of egg or tissue. The tissue can be, for example, muscle, skin, fat, kidney and liver. The tissue or egg is preferably finely particulated by fine grinding.

The gentian violet can be residual or added (spiked).

No fat extraction step (using a fat solvent) is necessary at all or before the acid-alcohol extraction step.

This process proceeds with an acid-alcohol extraction of the gentian violet from the tissue, egg, manure or feed. A known amount of acidified ethanol is admixed with the tissue, eggs, manure or feed, then the resultant admixture is let stand (preferably at room temperature in the dark for about 12 to 24 hours). Preferably the acidified alcohol contains 1 ml of the concentrated HCl per 100 ml of ethanol. Other acids, such as concentrated sulfuric acid and concentrated nitric acid, can be used in place of the concentrated HCl. The acidified alcohol is separated from the resultant admixture (preferably by centrifuging). (It is not necessary to repeat the acidified alcohol extraction step.)

Other suitable solvents can be used in place of the acidified ethanol. Straight ethanol is not a suitable alternative solvent for eggs and tissue since it only extracts at most about 50 percent of the gentian violet residue in eggs or tissue—acidified alcohol removes 99 percent or more of the gentian violet residue in eggs or tissue.

The acid ethanol extraction solution is passed through a chromatographic column to trap all of the interfering materials to provide a clear eluant for subsequent spectrophotometric analysis. The fatty substances are removed—the need to use a fat solvent is eliminated.

The gentian violet quenching step is achieved with a chemical substance which selectively renders the gentian violet non-detectable by spectrophotometric means without disturbing the spectrophotometric background of the acidified ethanol solvent solution. Such chemical substance only quenches the gentian violet.

The quenching agent has to be a strong oxidizing agent. The most preferred quenching agent is sodium hypochlorite (NaOCl). Other hypochlorites, such as calcium hypochlorite, potassium hypochlorite, barium hyochlorite, can be used as the quenching agent alkali metal and alkaline earth metal hypochlorites are particularly useful. The hypochlorites are useful because no salt is formed and hence no precipitation thereof. For example, the HCl in the acid-alcohol solvent reacts with a quenching agent such as NaOH to form NaCl, which precipitates leaving a cloudy solution. But NaOCl does not react with HCl to form a precipitating salt—it reacts with the gentian violet to render the gentian violet colorless.

The amount of quenching agent used is important. If too much quenching agent is used, the tissue will be oxidized and this will change the background. If too little quenching agent is used, not all of the gentian violet will be oxidized. So an effective amount of quenching agent, with such limits, is used.

If it is desired to measure the amount of gentian violet in a tissue sample in which the amount of gentian violet is completely unknown, a background reading is made. Then the quenching agent is added in increments until two identical readings are obtained. At this point it is known that all of the gentian violet has been quenched.

The procedure of this invention allows for the leaching of the protein bound gentian violet from the tissue samples with minimum background interference from other color components contained in the tissue samples. When the tissues are subjected to digestion in the appropriate solvent, the gentian violet is quantitatively released from the protein.

Gentian violet exhibits a characteristic absorption at 590 m$\mu$ which is suitable for the quantitative measurement of the compound.

To repeat, in this invention the gentian violet content of poultry tissues (for example) is determined spectrophotometrically. This procedure consists of acid alcohol digestion of the tissue samples to leach the gentian violet bound to the protein fraction of the tissues, passage of the solution through a chromatographic column to clarify it, and spectrophotometric measurement of the gentian violet content of the final solution. This treatment of the tissue samples serves to isolate the gentian violet from material present in the tissues which might interfere in the spectrophotometric measurement.

Preferably the steps of this process are conducted at room temperature and pressure, but higher and lower temperatures can be used.

The further improved analysis process of this invention gives a sensitivity as low as 1 or 2 ppb — the improved process of this invention has a lower sensitivity of at most 5 ppb. In the present state of quantitative analysis, this is an outstanding increase in sensitivity. The 1 or 2 ppb sensitivity is obtained when the basic sorbent for the chromatographic column is Alumin-SR, so the most preferred basic sorbent is Alumin-AR, and the neutralized ethanol solution is concentrated by a factor of at least tenfold.

After repeated pH studies it was found that when the acidified ethanol extract solution is passed through the chromatographic column to remove any spectrophotometrical interfering substance from the acidified ethanol extract solution, Alumin-AR sorbent in the chromatographic column neutralizes the acid portion of the acidified ethanol and the eluant delivered from the chromatographic column has a pH of approximately 7.2.

This neutral pH is particularly advantageous for determining minute quantities of gentian violet in the original acid ethanol extract solution since this neutral pH allows for concentration of the solution by evaporation to a smaller volume (for example, from 50 ml to 5 ml) thus concentrating the quantity of gentian violet in this smaller total volume — simple back calculation then allows for actual determination of the quantity of gentian violet (in ppm or ppb) that was present in the orginal acid ethanol extract solution used to remove the gentian violet from the sample in question.

The acid ethanol solution is necessary to most completely extract the gentian violet from the sample in question but this extract solution cannot be concentrated directly as the lower pH associated with concentration of the acid ethanol solution would destroy the gentian violet prior to spectrophotometric determination.

The acid portion of the acid ethanol extract solution is neutralized by the Alumin-AR sorbent in the chromatographic column and the extracted gentian violet remains in the ethanol portion of the extract then using a pH of 7.2 (i.e., essentially neutral pH). This neutral pH solution is then concentrated (by evaporation of the ethanol) to any desired volume (ordinarily 50 ml is concentrated to 5 ml) thus increasing the concentration of gentian violet in the smaller volume so that the amount of gentian violet in the original 50 ml of acid ethanol extract solution can be more readily determined spectrophotometrically to a higher degree of accuracy. After this determination, simple mathmatical back calculation can determine the amount of gentian violet (in ppm or ppb) present in the original 50 ml of acid ethanol extract solution.

Any convenient concentration method can be used to concentrate the neutralized ethanol solution.

The most preferred basic sorbent is Alumin-AR. Any other basic sorbent of a similar nature to Alumin-AR can be used in the chromatographic column, but such are not as effective in neutralization of the acid portion of the acidic ethanol extract solution. A preferred class of basic sorbents are the activated aluminum oxides taught on page 46 of The Merck Index, 8th Ed., (1968) — such information is incorporated herein by reference.

The analysis method of this invention can also be used to quantitatively determine the presence of any substituted benzophenone azoanilide dyes or rosaniline base dyes other than the gentian violet in tissue, eggs, feed or manure, provided such other dye can be removed from the tissue, eggs, feed or manure by the acid — ethanol solvent. Such other dyes are also known as triaminotritane dyes related to rosaniline. The —N(CH$_3$)$_2$ groups can be replaced with other auxochrome groups such as —OH, —NH$_2$, —N(C$_2$H$_5$)$_2$, etc.

The other various substituents, and the substituents on gentian violet, can be located at any position on the three benzyl rings. The other dyes must have at least one amino chloride group and/or substituted amino chloride group.

Examples of such other substituted benzophenone azoanilide dyes are: pentamethylpararosaniline chloride; tetramethylparosaniline chloride; methyl green or light green, which is the methyl chloride addition product of gentian violet; ethyl green, which is the ethyl chloride addition product of gentian violet; sulfonic acids of the rosanilines, such as, water blue and patent blue; phenylated rosanilines, such as, triphenyl fuchsin, aniline blue, diphenylamine blue and spirit blue; pararosaniline; mixtures of pararosaniline with its methyl homologs, such as fushins and magentas. More broadly, any triphenylmethane dye, or for that matter any dye that contains an amino group or substituted amino group can be quantitatively determined as long as it can be removed from the tissue, feed, eggs or manure by the acid — ethanol solvent. Examples of such triphenylmethane dyes are the malachite green series of dyes, such as, malachite green.

Most of such aniline dyes are rather toxic, but can be readily used in feeds, etc. if they are buffered by any generally non-toxic conventional buffering system to reduce their toxicity.

All parts, percentages and ratios are on a weight basis, unless otherwise stated or otherwise obvious herefrom to one ordinarily skilled in the art.

EXAMPLE 1

This example involves the spectrophotometrical determination of the gentian violet content (as a residue) of poultry tissue.

The following reagents were used:
a. alcohol, ethyl — 95 percent denatured EX 280, L 376, Matheson, Coleman and Bell.
b. acid, hydrochloric, concentrated — R. G., J. T. Baker.
c. Alumin AR O 100 to 200 mesh, activity Grade-4, chromatographic Sorbent, Mallinckrodt Chemical Works.
d. water, distilled.
e. 0.26 percent aqueous sodium hypochlorite solution.

The apparatus included: a Waring blender, variable speed; an analytical balance — Ainsworth chainomatic type LCB; an analytical balance — Mettler type P162; glass beakers — 50 to 100 ml capacity; a spectrum glass spatula — 8inches ; volumetric pipettes -0.01 ml. 0.1 ml, 0.5 ml, 1.0 ml and 5.0 ml; a magnetic mixer; magnetic stirring bars — ¾inches; centrifuge tubes — 60 ml glass; centrifuge — speed to 3,000 rpm — capable of accommodating 60 ml tubes; graduated cylinders — 50 ml; Erlenmeyer flasks, 125 ml with ground glass stoppers; turner spectrophotometer; 13 mm matched cuvetts; spectrophotometer — Beckman D.U. quartz — with attachment for 100 mm cells; spectrophotometer cells — 100 mm — Beckman 580021; and chromatographic columns — 10 mm Fabco No. 4280 with 100 ml reservoir (or equivalent) equipped with stopcock.

All phases of the analytic procedure of this invention must be conducted under conditions of diffused light. Gentian violet is extremely sensitive to decomposition by the ultra violet rays of sunlight. In this example, the laboratory was illuminated entirely by artificial light, with the source of light at least 2 meters away from the work areas.

The tissue samples were protected from excess heat, as heat crystallizes the tissues and imparts excess background color to the extraction solutions. All procedures of this example were carried out at room temperature (68° to 72° F.).

An acid alcohol solution was prepared by adding 20 ml of concentrated hydrochloric acid to 2,000 ml of 95 percent ethyl alcohol (denatured).

A gentian violet stock solution was prepared as follows: Using the Ainsworth chainomatic analytical balance, 0.104 gm of crystalline gentian violet (USP) was accurately weighed out and quantitatively transferred to a 1000 ml volumetric flask and q.s. to 1000 ml with distilled water. A magnetic stirring bar was inserted into the flask and the gentian violet solution was mixed on a magnetic mixer for 1 hour. This solution contained 100 ug of gentian violet per ml (100 ppm).

Gentian violet-acid alcohol standard solutions were prepared as follows: Five standard dilutions of gentian violet in acid alcohol were prepared and the absorbence (O.D.) for each dilution was determined. The absorbence of the 5 dilutions were plotted on a graph to determine the linearity of the gentian violet curve.

2 ml of 100 ppm aqueous g.v. solution q.s. to 100 ml with ac-EtOH = 2 ppm 1.5 ml of 100 ppm aqueous g.v. solution q.s. to 100 ml with ac-EtOH = 1.5 ppm 1.0 ml of 100 ppm aqueous g.v. solution q.s. to 100 ml with ac-EtOH = 1.0 ppm 0.5 ml of 100 ppm aqueous g.v. solution q.s. to 100 ml with ac-EtOH = 0.5 ppm 0.1 ml of 100 ppm aqueous g.v. solution q.s. to 100 ml with ac-EtOH = 0.1 ppm.

The spectrophotometer was set at 590 m$\mu$ and zeroed using an acid alcohol blank. The absorbence of the 5 standard dilutions in the 13 mm cuvette was determined. The O.D. of the 1 ppm dilution in the 13 mm cuvette was recorded for use in calculation of the gentian violet recovery. (If method sensitivity below 0.1 ppm is desired, the O.D. of the 1 ppm standard in the 100 mm cell is recorded and the Beckman D.U. is used to made the determinations.)

A sodium hypochlorite quenching solution was prepared as follows: 0.26 gm. of sodium hypochlorite was weighed into a 250 ml Erlenmeyer flask and q.s. to 100 ml with distilled water. This solution was 0.26 percent NaOCL. If sodium hypochlorite is not available in the laboratory, this solution can be made from any standard household bleaching solution containing sodium hypochlorite (i.e., Clorox) at the 5.25 percent concentration. 1 ml 5.25 percent NaOCL q.s. to 20 ml with distilled water to give 20 ml of 0.26 percent NaOCL.

The tissue samples were prepared by grinding the tissues in a Waring-type blender to reduce the tissues to the smallest particle size possible. Using a Mettler P162-type balance, 5 gm samples of the finely ground tissues were weighed (in triplicate) into Erlenmeyer flasks.

Gentian violet was extracted from tissue samples as follows: 50 ml of acid-alcohol were added (using a graduated glass cylinder) to each of the samples in the flasks. A ¾ inches magnetic stirring bar was inserted into each sample. The flasks were stoppered. The samples were placed on the magnetic mixers and mixed for 1 hour. After mixing, the samples were set in the dark to digest for 12 hours (overnight). After 12 hours of digestion the samples were again placed on the magnetic mixer and mixed for 1 hour. The contents of the sample flasks were poured into 60 ml glass centrifuge tubes and centrifuged at 2400 rpm for 10 minutes.

Chromatographic column clearing of the centrifuged samples was achieved as follows: Each column was equipped with a glass stop-cock, if the column was not so equipped. A small glass-wool pledget was inserted firmly in the bottom of the column to fill the bottom curve of the column. 5 to 6 grams of the Alumin AR sorbent was added to each column. The supernatant liquid was carefully decanted from the centrifuge tube into the chromatographic column. A 50 ml beaker was placed under each column. The stop-cock was opened and the first eluant from the column was collected until a minimum of 20 ml was collected. (This first eluant ordinarily was yellow in color but contained the extracted gentian violet.)

Spectrophotometric determination of the gentian violet concentration from the tissue sample was determined as follows: 5 ml of each of the eluants was pipetted into the 13 mm cuvettes. The spectrophotometer was set at 590 mu. The spectrophotometer was zeroed using an acid alcohol blank in the 13 mm cuvette. It was established that all cuvettes were matched. The absorbence of each of the samples was read and the optical density (O.D.) reading was recorded. After the initial absorbence was determined and recorded, 0.01 ml of the 0.26 percent NaOCL solution was pipetted into each sample cuvette. The cuvettes were stoppered and shaken for 10 to 15 seconds to quench the gentian violet in the test solutions. The spectrophotometer was zeroed again with the acid-alcohol blank and the absorbence of the quenched solutions was read. The O.D. of each of the quenched solutions was recorded.

At any time, after passage of the extract solution through the chromatographic column, the solution appeared cloudy, the solution was warmed in a water bath for 1 to 2 minutes and the cloudiness disappeared.

The absorbence of the sample solutions was identified by the following symbols:

Sample Identity: Absorbence Code
Prequenched O.D.: $A_x$
Quenched O.D.: $A_q$.

Calculation of gentian violet recovery from tissue samples in as follows:

$$\text{Sample} = \frac{A_x - A_q}{A_k} \times M_1 =$$

ug of gentian violet recovered from tissue
wherein:

$A_x$ = absorbence at 590 m$\mu$ of unquenched solution.
$A_q$ = absorbence at 590 m$\mu$ of quenched solution.
$A_k$ = absorbence at 590 m$\mu$ of 1 ppm of gentian violet — acid alcohol standard solution.
$M_1$ = ml of acid alcohol used to extract gentian violet from the tissue samples (10 ml/gm of tissue sample).

And:

$$\frac{\text{ug gentian violet recovered}}{\text{grams of sample extracted}} = \text{ug/g} = \text{ppm recovered}.$$

A sample calculation is:

$A_x$ = 0.042 O.D.

$A_q = 0.040$ O.D.
$A_k = 0.250$ O.D.
$M_1 = 50$ ml of acid-alcohol.

$$\frac{A_x - A_q}{A_k} \times M_1 = \text{ug recovered.}$$

$$\frac{0.042 - 0.040}{0.250} \times 50 \text{ ml} = 0.40 \text{ ug of gentian violet recovered.}$$

$$\frac{0.40 \text{ ug}}{5 \text{ g}} = 0.08 \text{ ug/g} = 0.08 \text{ ppm of gentian violet recovered.}$$

EXAMPLES 2 to 24

Example 1 was repeated 23 times using chicken liver samples from chickens which had been fed feed which contained gentian violet. (A number of chicken liver control samples, i.e., from chickens which had been fed feed which did not contain any gentian violet, were also run using the procedure of Example 1.) Livers have been found to have the highest gentian violet residues.

The broiler chickens had been split into three groups. Group 1 (Examples 2 to 9) was fed feed having 0 ppm of gentian violet. Group 2 (Examples 10 to 16) was fed feed having 7 ppm of gentian violet. Group 3 (Examples 17 to 24) was fed feed having 35 ppm of gentianl violet. All of the chickens were fed for 56 days. The chickens of Examples 2, 3, 10, 17 and 18 were sacrificed 4 hours after the final does of gentian violet. The chickens of Examples 4, 5, 12, 19 and 20 were sacrificed 12 hours after the final dose of gentian violet. The chickens of Examples 6, 7, 13, 14, 21 and 22 were sacrificed 24 hours after the final dose of gentian violet. The chickens of Examples 8, 9 15, 16, 23 and 24 were sacrificed 48 hours after the final dose of gentian violet.

The control samples of Examples 2 to 9 and the samples of Examples 10 to 16 were quenched with 0.01 ml of 0.26 percent sodium hypochlorite. The samples of Examples 17 to 24 were quenched with 0.05 ml of 0.26 percent sodium hypochlorite. The optical density of the 1 ppm HC1-ethanol standard repeatedly was 0.250.

Table I

| Example Number | Optical Density | Quenched Optical Density | p.p.m. of Gentian Violet |
|---|---|---|---|
| 2 | 0.070 | 0.070 | 0.00 |
|   | 0.075 | 0.075 | 0.00 |
|   | 0.075 | 0.075 | 0.00 |
| 3 | 0.048 | 0.048 | 0.00 |
|   | 0.051 | 0.051 | 0.00 |
|   | 0.048 | 0.048 | 0.00 |
| 4 | 0.039 | 0.039 | 0.00 |
|   | 0.039 | 0.039 | 0.00 |
|   | 0.031 | 0.031 | 0.00 |
| 5 | 0.047 | 0.047 | 0.00 |
|   | 0.041 | 0.041 | 0.00 |
|   | 0.045 | 0.045 | 0.00 |
| 6 | 0.083 | 0.083 | 0.00 |
|   | 0.080 | 0.080 | 0.00 |
|   | 0.082 | 0.082 | 0.00 |
| 7 | 0.078 | 0.078 | 0.00 |
|   | 0.081 | 0.081 | 0.00 |
|   | 0.089 | 0.089 | 0.00 |
| 8 | 0.060 | 0.060 | 0.00 |
|   | 0.060 | 0.060 | 0.00 |
|   | 0.055 | 0.055 | 0.00 |
| 9 | 0.060 | 0.060 | 0.00 |
|   | 0.051 | 0.051 | 0.00 |
|   | 0.060 | 0.060 | 0.00 |
| 10 | 0.029 | 0.023 | 0.24 |
|   | 0.035 | 0.028 | 0.28 |
|   | 0.031 | 0.024 | 0.28 |
| 11 | 0.031 | 0.024 | 0.28 |
|   | 0.029 | 0.022 | 0.28 |
|   | 0.031 | 0.024 | 0.28 |
| 12 | 0.038 | 0.035 | 0.12 |
|   | 0.051 | 0.048 | 0.12 |
|   | 0.040 | 0.037 | 0.12 |
| 13 | 0.095 | 0.093 | 0.08 |
|   | 0.100 | 0.095 | 0.20 |
|   | 0.090 | 0.087 | 0.12 |
| 14 | 0.102 | 0.098 | 0.16 |
|   | 0.103 | 0.102 | 0.04 |
|   | 0.095 | 0.090 | 0.20 |
| 15 | 0.053 | 0.051 | 0.08 |
|   | 0.048 | 0.045 | 0.12 |
|   | 0.061 | 0.058 | 0.12 |
| 16 | 0.042 | 0.040 | 0.08 |
|   | 0.051 | 0.048 | 0.12 |
|   | 0.050 | 0.046 | 0.16 |
| 17 | 0.060 | 0.041 | 0.84 |
|   | 0.063 | 0.041 | 0.88 |
| 18 | 0.073 | 0.056 | 0.068 |
|   | 0.073 | 0.055 | 0.72 |
| 19 | 0.051 | 0.040 | 0.44 |
|   | 0.048 | 0.037 | 0.44 |
| 20 | 0.028 | 0.017 | 0.44 |
|   | 0.022 | 0.011 | 0.44 |
| 21 | 0.041 | 0.025 | 0.64 |
|   | 0.076 | 0.056 | 0.80 |
| 22 | 0.068 | 0.053 | 0.60 |
|   | 0.051 | 0.036 | 0.60 |
| 23 | 0.047 | 0.038 | 0.36 |
|   | 0.050 | 0.041 | 0.36 |
| 24 | 0.081 | 0.075 | 0.24 |
|   | 0.076 | 0.070 | 0.24 |

Table I demonstrates that the quenching agent NaOCl, in the amounts used, only quenches the gentian violet. This fact is demonstrated by the absorbence readings of the liver samples of the control birds (see Table I) in which no change of O.D. is found when the quenching solution is added to the control eluant. (The sensitivity of the analytical method, using the 13 mm cuvette, is such that 0.04 ppm gentian violet can be detected in the eluant. Use of the Beckman D.U. spectrophotometer equipped with the 100 mm cell, enables detection of gentian violet residues to approximately 0.005 ppm.)

The results of Table I show that the gentian violet residue is lower with time after the last intake of feed which contains gentian violet.

EXAMPLE 25

Example 1 was repeated using a chicken liver control sample. The analysis was run without knowing a control sample was involved. The quenching was done with 0.01 ml of 0.26 percent sodium hypochlorite. The tissue analysis results for the control sample (four separate batches or runs) is:

Table II

| Optical Density | Quenched Optical Density | ppm of Gentian Violet |
|---|---|---|
| 0.065 | 0.065 | 0.00 |
| 0.058 | 0.058 | 0.00 |
| 0.070 | 0.070 | 0.00 |
| 0.038 | 0.038 | 0.00 |

EXAMPLE 26

This example was run to determine that the liver was the target tissue (i.e., had the highest gentian violet residue), and that the quenching technique of this invention was accurate. The residual levels of gentian violet in parts per million (ug/g) in kidneys and livers taken from sacrificed young chickens after repeated oral administrations of $^{14}C$-gentian violet was determined.

The specific activity of the 14$_C$-gentian violet (or crystal violet) was determined to be 5.8 ± 0.2 uCi/mg. (Another source determined the specific activity to be 5.99 uCi/mg.)

Thirty-six animals, 7 day old male cockerels, were received and housed in a galvanized steel, wire-bottom rabbit cage. Water and chicken starter feed was provided ad libitum. Five days after being received, 33 chicks were selected and individually housed in galvanized steel, wire-bottom rat cages.

An aqueous solution of $^{14}$C-gentian violet was prepared by dissolving 50.4 mg of the compound in water and bringing the solution to volume in a 100 ml volumetric flask. The lower dose level was prepared by diluting 20 ml of the 0.5 mg/ml solution to 100 ml with distilled water. The second dose was referred to as the 1X dose level. The first solution was referred to as the 5X dose level.

Each administration of each dose was performed by drawing the preparation into a 1 ml disposable Tuberculin Plastipak™ syringe fitted with a No. 20 gavage needle; removing air bubbles from syringe and needle; filling the syringe to the appropriate volume; inserting the gavage needle into the animal's esophagus (covering the needle to the hub) and dispensing the preparation into the gastro-intestinal tract. Each chicken was weighed prior to dosing. If the animal weighed more than 100 gm, 0.25 or 0.05 mg $^{14}$C-gentian violet was administered. If the animal weighed less than 100 gm, the appropriate dose level was prorated according to the animal's weight. Thus, an animal weighing less than 100 gm and receiving the 5X dose received 2.5 mg $^{14}$C-gentian violet per kg; an animal weighing less than 100 gm and receiving the 1X dose received 0.5 mg $^{14}$C-gentian violet per kg.

The preparations were administered on 12 consecutive days at 8:30 AM. The 5X dose was administered to 20 birds, and the 1X dose was administered to 13 birds. The chickens were numbered from 1 to 33 and sacrificed at 4, 12, 24, 48 and 72 hours after administering the last dose.

Each chicken to be sacrificed was anesthetized with ether and exsanguinated from the jugular vein using a syringe flushed with an aqueous solution of 0.5 mg sodium heparin U.S.P./ml distilled water. After the animal died, the abdominal cavity was exposed and the duct between the liver and the gall bladder was tied off. The liver was then removed, cutting the bile duct between the liver and the knot. The kidneys were then removed.

Both organs were weighed after being removed from the body. Immediately after weighing, duplicate aliquots of each organ were weighed into Combusto-Cones™ (Cat. No. 5065913; Packard Instrument Co.; Downers Grove, Illinois). Aliquots weighed between about 160 and 380 mg. The remainder of each organ was placed in a capped scintillation vial and frozen.

All aliquots of organs were air-dried; the paper cones were tightly folded and samples were combusted in a Packard Model 305 Tri-carb Sample Oxidizer. The $^{14}$C module of the oxidizer was calibrated to deliver methanol, ethanolamine, and scintillation cocktail in a ratio of 9:5:6 into the scintillation vial. Performance checks (Manual 2118, Packard Instrument Company, pp. 208 to 2-10) were performed each day samples were combusted. A mean recovery of at least 95.0 percent and a memory of no more than 0.05 percent was required before samples were oxidized. A determination of oxidizer blank $^{14}$C trapping efficiency, and memory were also performed after oxidizing samples. $^{14}$C activity in samples prepared by oxidation was corrected for the oxidizer blank and the trapping efficiency. The scintillator for the oxidizer was 0.8 percent Preblend 2a60 in toluene (w/v). Preblend 2a60 is a preblended fluor composed of 91 percent PPO:2,5-diphenyloxazole and 9 percent POPOP:1,4-bis-2-(5-phenyloxazolyl)-benzene.

All liquid scintillation determinations of $^{14}$C activity were made with a Searle Analytic Mark I Model 8725 liquid scintillation system. Counting efficiency for samples was determined by the external standard channels ratio method. The channel attentuator settings were: Channel A-A, 870; Channel B-E, 760; and Channel C-B-O. Quench curves were plotted from the B/A ratio versus counting efficiencies of sealed standards containing a known amount of $^{14}$C activity and varying degrees of quenching. Sample counting efficiencies were found on the standard quench curve corresponding to the sample B/A counted with the external standard. All samples and blanks were counted for 10 minutes.

Net cpm (counts per minute) for each sample was computed by subtracting the blank cpm from the sample's gross cpm. Net cpm was divided by scintillation counter efficiency to compute dpm (disintegrations per minute). Sample dpm were divided by oxidizer trapping efficiency to correct for oxidizer performance. Dpm/gram of sample was calculated by dividing corrected sample dpm by the sample aliquot weight (in grams). The concentration of ug $^{14}$C-gentian violet per gram of tissue (ppm) was computed by dividing the sample dmp/gm by $13.29 \times 10^6$ dpm per mg $^{14}$C-gentian violet. This result was multiplied by 1000 to convert mg. to ug, thereby giving ppm. Totol dpm for an organ was computed by multiplying dpm/gram by the weight of the organ in grams.

Eighteen aliquots (0.2 gm) were taken of a fresh liver from a 15 day-old chick, and each aliquot was weighed into a tared Combusto-Cone™; the chick was exposed to no radioactive dose. Five sets of three aliquots were spiked, with 10, 50 and 100 ul Hamilton syringes, with varying amounts of an ethanolic solution of $^{14}$C-gentian violet to give concentrations of 1, 3.75, 7.5, 19 and 38 nanograms $^{14}$C-gentian violet per gram of tissue (ppb). The samples were air-dried at room temperature, oxidized, and counted for ten minutes according to the procedures described above. The dpm per gram and nanograms per gram (ppb) were computed for each of the eighteen samples.

Table III sets out the mean residues of $^{14}$C-gentian violet in livers and kidneys for the 2.5 mg/kg (5X) and the 0.5 mg/kg (1X) dose levels. The amounts of $^{14}$C-gentian violet found in each individual tissue are set out in Table IV. The relative variation among samples taken at one time, as measured by the percentage of standard error of the mean (percent S.E.M.), is greater for the livers than for the kidneys. An unusually high concentration of $^{14}$C-gentian violet was found in the liver of chick no. 31 sacrificed at 72 hours after administering the last dose. The high concentration of radioactivity can partially be explained by the low organ weight. Contamination from a ruptured bile duct is also possible; however, whenever the bile duct did burst during the necropsy, the liver was carefully washed with a small volume of distilled water. The kidney of this chick also has a high concentration of radioactivity.

Table III

Mean Tissue Residues of Gentian Violet After Oral Administrations of $^{14}$C-Gentian Violet (with Standard Errors of the Mean)

| Post-Dose Time | 5X Dose Liver (ppm) | 5X Dose Kidneys (ppm) | 1X Dose Liver (ppm) | 1X Dose Kidneys (ppm) |
|---|---|---|---|---|
| 4 hrs. | 0.779 | 0.477 | 0.284 | 0.102 |
| S.E.M. | 0.084 | 0.078 | 0.075 | 0.018 |
| % S.E.M. | 11 | 16 | 35 | 8 |
| 12 hrs. | 0.500 | 0.267 | 0.120 | 0.079 |
| S.E.M. | 0.156 | 0.037 | 0.048 | 0.019 |
| % S.E.M. | 31 | 14 | 23 | 24 |
| 24 hrs. | 0.679 | 0.210 | 0.114 | 0.067 |
| S.E.M. | 0.162 | 0.036 | 0.051 | 0.022 |
| % S.E.M. | 24 | 17 | 45 | 33 |
| 48 hrs. | 0.275 | 0.104 | 0.102 | 0.039 |
| S.E.M. | 0.060 | 0.015 | 0.005 | 0.001 |
| % S.E.M. | 22 | 14 | 5 | 3 |
| 72 hrs. | 0.686* | 0.150* | 0.034 | 0.024 |
| S.E.M. | 0.021** | 0.006** | 0.007 | 0.002 |
| % S.E.M. | 10 | 8 | 21 | 8 |

Notes:
*A sport, high value among three liver and kidney samples taken at this time. Mean of two liver values is 0.205. Kidney samples: 0.073.
**S.E.M. based on two samples.

Table IV

$^{14}$C In Cockerel Organs Four Hours After Administration of $^{14}$C-Gentian Violet

| Sample | Organ Weight (gm) | dpm/ Organ | dpm/ gram | ug/gram (ppm) |
|---|---|---|---|---|
| 5X Dose | | | | |
| Liver No. | | | | |
| 22 | 3.215 | 44,618 | 13,878 | 1.044 |
| 15 | 5.133 | 50,607 | 9,859 | 0.742 |
| 16 | 5.330 | 42,844 | 8,038 | 0.605 |
| 17 | 4.834 | 46,652 | 9,651 | 0.726 |
| Kidneys No. | | | | |
| 22 | 1.216 | 11,116 | 9,183 | 0.691 |
| 15 | 1.923 | 9,227 | 4,798 | 0.361 |
| 16 | 1.875 | 8,867 | 4,729 | 0.356 |
| 17 | 1.878 | 12,505 | 6,658 | 0.501 |
| 1X Dose | | | | |
| Liver No. | | | | |
| 1 | 7.070 | 21,804 | 3,084 | 0.232 |
| 2 | 6.306 | 36,280 | 5,753 | 0.433 |
| 3 | 6.548 | 16,323 | 2,493 | 0.188 |
| Kidneys No. | | | | |
| 1 | 2.395 | 2,863 | 1,184 | 0.089 |
| 2 | 2.613 | 4,271 | 1,634 | 0.123 |
| 3 | 1.790 | 2,272 | 1,269 | 0.095 |

$^{14}$C in Cockerel Organs Twelve Hours After Administration of $^{14}$C-Gentian Violet

| Sample | Organ Weight (gm) | dpm/ Organ | dpm/ gram | ug/gram (ppm) |
|---|---|---|---|---|
| 5X Dose | | | | |
| Liver No. | | | | |
| 18 | 5.630 | 66,438 | 11,801 | 0.888 |
| 19 | 6.033 | 24,948 | 4,135 | 0.311 |
| 20 | 6.170 | 17,753 | 3,201 | 0.241 |
| 21 | 6.972 | 26,299 | 3,772 | 0.284 |
| 23 | 6.611 | 68,033 | 10,291 | 0.774 |
| Kidneys No. | | | | |
| 18 | 2.274 | 11,939 | 5,250 | 0.395 |
| 19 | 2.086 | 6,796 | 3,258 | 0.245 |
| 20 | 2.136 | 6,537 | 3,060 | 0.230 |
| 21 | 2.447 | 5,712 | 2,334 | 0.176 |
| 23 | 2.027 | 7,815 | 3,855 | 0.290 |
| 1X Dose | | | | |
| Liver No. | | | | |
| 4 | 5.500 | 5,477 | 996 | 0.075 |
| 5 | 6.357 | 5,889 | 927 | 0.070 |
| 6 | 6.715 | 19,188 | 2,857 | 0.215 |
| Kidneys No. | | | | |
| 4 | 2.130 | 1,746 | 820 | 0.062 |
| 5 | 2.172 | 1,696 | 764 | 0.057 |
| 6 | 2.211 | 3,452 | 1,561 | 0.117 |

$^{14}$C in Cockerel Organs Twenty-Four Hours After Administration of $^{14}$C-Gentian Violet

| Sample | Organ Weight (gm) | dpm/ Organ | dpm/ gram | ug/gram (ppm) |
|---|---|---|---|---|
| 5X Dose | | | | |
| Liver No. | | | | |
| 24 | 6.289 | 60,300 | 9,588 | 0.721 |
| 25 | 6.158 | 67,384 | 10,942 | 0.823 |
| 26 | 5.351 | 68,033 | 12,714 | 0.957 |
| 27 | 7.267 | 20,674 | 2,845 | 0.215 |
| Kidneys No. | | | | |
| 24 | 2.060 | 6,185 | 3,002 | 0.226 |
| 25 | 2.176 | 6,443 | 2,961 | 0.223 |
| 26 | 1.950 | 7,315 | 3,751 | 0.282 |
| 27 | 2.476 | 3,623 | 1,463 | 0.110 |
| 1X Dose | | | | |
| Liver No. | | | | |
| 7 | 5.047 | 14,586 | 2,890 | 0.217 |
| 8 | 6.222 | 5,165 | 830 | 0.062 |
| 9 | 8.519 | 7,248 | 851 | 0.064 |
| Kidneys No. | | | | |
| 7 | 1.848 | 2,705 | 1,463 | 0.110 |
| 8 | 2.318 | 1,481 | 639 | 0.048 |
| 9 | 2.930 | 1,644 | 561 | 0.042 |

$^{14}$C in Cockerel Organs Forty-Eight Hours After Administration of $^{14}$C-Gentian Violet

| Sample | Organ Weight (gm) | dpm/ Organ | dpm/ gram | ug/gram (ppm) |
|---|---|---|---|---|
| 5X Dose | | | | |
| Liver No. | | | | |
| 28 | 5.788 | 15,334 | 2,649 | 0.199 |
| 29 | 5.206 | 27,176 | 5,220 | 0.393 |
| 30 | 4.390 | 13,617 | 3,102 | 0.233 |
| Kidneys No. | | | | |
| 28 | 2.237 | 2,197 | 982 | 0.074 |
| 29 | 2.276 | 3,750 | 1,647 | 0.124 |
| 30 | 1.911 | 2,882 | 1,508 | 0.113 |
| 1X Dose | | | | |
| Liver No. | | | | |
| 10 | 5.917 | 8,396 | 1,419 | 0.107 |
| 11 | 4.701 | 6,073 | 1,292 | 0.097 |
| Kidneys No. | | | | |
| 10 | 2.321 | 1,186 | 511 | 0.038 |
| 11 | 1.638 | 863 | 527 | 0.040 |

$^{14}$C in Cockerel Organs Seventy-Two Hours After Administration of $^{14}$C-Gentian Violet

| Sample | Organ Weight (gm) | dpm/ Organ | dpm/ gram | ug/gram (ppm) |
|---|---|---|---|---|
| 5X Dose | | | | |
| Liver No. | | | | |
| 31 | 2.079 | 45,587 | 21,927 | 1.650 |
| 32 | 4.491 | 10,991 | 2,447 | 0.184 |
| 33 | 4.428 | 13,245 | 2,991 | 0.225 |
| Kidneys No. | | | | |
| 31 | 1.236 | 4,998 | 4,044 | 0.304 |
| 32 | 2.084 | 1,843 | 844 | 0.067 |
| 33 | 1.720 | 1,792 | 1,042 | 0.078 |
| 1X Dose | | | | |
| Liver No. | | | | |
| 12 | 11.982 | 7,261 | 546 | 0.041 |
| 13 | 10.383 | 3,744 | 361 | 0.027 |
| Kidneys No. | | | | |
| 12 | 2.916 | 972 | 333 | 0.025 |
| 13 | 2.627 | 759 | 289 | 0.022 |

When the data in Table III is plotted in a two-cycle semilogrithmic (Y-axis) scale, a plot of the best fit of log of concentration vs. time to a straight line can be achieved. The mean concentrations of gentian violet oscillate around the idealized elimination curves; in most cases up to 24 hours, the idealized curve passes within the range of the standard error of the mean. Table V presents the elimination rate constants and the half-lives of gentian violet computed from the linear regression curve of the data. The correlation coefficient for each linear regression is also given in Table V.

The data indicate that gentian violet is concentrated about twice as much by the liver as by the kidneys. Comparing the results from the 5X and 1X does indicates that the concentrating action of each organ decreases when the dose increases. At four hours after the last administration of the compound, there is 2.7 times as much radioactivity in the 5X livers as in the 1X livers; there is 4.7 times as much radioactivity in the 5X kidneys as in the 1X kidneys. The mean half-life of gentian violet in the two organs at dose levels is 32.2 hours. The compound does not disappear more rapidly from one organ than the other.

Table V

Disappearance Rates of $^{14}$C-Gentian Violet From Livers and Kidneys

|  | Elimination Rate Constant (Ke) (hr-1) | Half-Life (t½) (hours) | Correlation Coefficient |
|---|---|---|---|
| 5X Dose |  |  |  |
| Livers | −0.0193 | 35.9 | 0.935 |
| Kidneys | −0.0262 | 26.7 | 0.974 |
| 1X Dose |  |  |  |
| Livers | −0.0247 | 28.0 | 0.959 |
| Kidneys | −0.0209 | 38.0 | 0.998 |

A comparison of the chemical method residues (see Examples 2 to 24) to the C-14 residues demonstrates that the residue levels in livers from birds dosed "lifetime" with cold gentian violet very closely approximate the residue levels in the C-14 studies for all post-dose periods tested.

Examination of the data in the C-14 study indicates the following tissue residues to be present at 72 hours post-dose:

| Sample | Residue 72 hrs. post-dose |
|---|---|
| Liver | 0.034 ppm |
| Kidney | 0.024 ppm |
| Skin/fat | 0.016 ppm |
| Breast muscle | 0.012 ppm |
| Thigh muscle | 0.012 ppm |
| Gizzard muscle | 0.002 ppm |
| Heart muscle | 0.007 ppm |

It would appear from the close correlation of the chemical method residue results with the C-14 study that it could be expected, with a reasonable withdrawal time of 3 to 5 days, that the residue in the target tissue (liver) would be at or below the lowest detection capability of the chemical residue method (0.04 ppm) and would be approaching zero residue by 5 days withdrawal.

Example 27

Example 26 was repeated using spiked tissues (chick) instead of tissue taken from chicks fed feed which contained gentian violet. The results of the experiments with spiked tissue samples are presented in Table VI.

The 95 percent confidence limit was computed by multiplying the standard deviation by the value for Student's t-ratio (4.303) for 95 percent confidence limit and 2 degrees of freedom. The mean dpm/gram for the unspiked samples falls within the 95 percent confidence range of the first two spike levels. This indicates that by the criteria of 95 percent confidence limits, the detection limit is above 4 ppb, i.e., 10 dpm.

This result corresponds to a detection limit of twice the background, since the dpm/gm for 7.5 dpm is about two times the dpm/gm for unspiked tissue.

Table VI

Detection of $^{14}$C-Gentian Violet in Spiked Liver Samples

| Volume of Standard | Activity Added | | Mean dpm/ Sample | Mean dpm/g | ± 95% Confidence Limit (dpm/g) | Lower Confidence Limit (dpm/g) |
|---|---|---|---|---|---|---|
|  | dpm | dpm/g |  |  |  |  |
| 0 | 0 | 0 | 41.1 | 203 | ± 102 | — |
| 3.63 | 2.7 | 13.7 | 55.4 | 283 | ± 196 | 87 |
| 13.5 | 10 | 50.7 | 65.5 | 331 | ± 136 | 195 |
| 26.9 | 20 | 97 | 82.2 | 400 | ± 72 | 328 |
| 67.3 | 50 | 266 | 114.8 | 608 | ± 296 | 312 |
| 134.6 | 100 | 522 | 201.0 | 1049 | ± 652 | 397 |

EXAMPLE 28

In order to check the sensitivity of the methodology of this invention the instrumentation accuracy of instruments, etc., used in Examples 2 to 24, such was repeated using the chicken tissue spiked at the following gentian violet levels:

0.1 ppm
0.01 ppm
0.02 ppm
0.03 ppm
0.04 ppm
0.05 ppm
0.005 ppm.

Sensitivity in the 13 mm cell was shown to be 0.04 ppm.

Sensitivity in the 100 mm cell was shown to be 0.005 ppm.

EXAMPLE 29

Example 1 was repeated, except that ethanol solution (neutralized) was concentrated by a factor of ten before it was quenched with sodium hypochlorite. Also, the 13 mm curvette was used with the spectrophotometer. The sensitivity of the analysis was 2 ppb of gentian violet.

The pH of the acid ethanol tissue extract solution (containing the extracted gentian violet) was approximately 2.2. If evaporation and concentration of this strongly acid solution was attempted directly the pH would be lowered to a point where the acid would destroy the extracted gentian violet.

The Alumin-AR sorbent, 100–200 mesh, grade 4, is prepared from carefully screened aluminum hydroxide and has a pH of approximately 9.3 in a slurry form (i.e., when a liquid is poured into the chromatographic column and passed through the dry Alumin-AR sorbent). The 9.3 pH of the aluminum hydroxide (Alumin-AR sorbent) is particularly suitable to neutralize the HCl portion of the acid ethanol tissue extract solution — the neutralized eluant delivered from the chromatographic column has a pH of approximately 7.2. This neutralized eluant is concentrated (by evaporation of the ethanol) to a lower total volume (i.e., 50 ml to 5 ml), which increases the gentain violet/per ml concentration to facilitate more accurate tissue extract gentian violet concentrations. The eluant was neutralized by the passage of the acid ethanol extract solution through the Alumin-AR sorbent. What transpired in the column was a typical acid base neutralization and the eluant was delivered from the column in neutral solution ready for evaporation (concentration). This allowed an increase in sensitivity to two ppb of gentian violet.

EXAMPLE 30

Example 2 was repeated, except that the ethanol solution (neutralized) was concentrated by a factor of 10 before it was quenched with sodium hypochlorite. Also, the 13 mm curvette was used with the spectophotometer. The sensitivity of the analysis was 2 ppb of gentian violet.

EXAMPLE 31

In order to check the sensitivity of the methodology of this invention the instrumentation accuracy of instruments, etc., used in Example 30, such was repeated using the chicken tissue spiked at the following gentian violet levels:

0.1 ppm
0.01 ppm
0.02 ppm
0.03 ppm
0.04 ppm
0.05 ppm
0.005 ppm (5ppb)
0.002 ppm (2 ppb).

Sensitivity in the 13 mm cell was shown to be 0.002 ppm (2ppb).

All of the numbered examples used a basic sorbent (i.e., Alumin-AR), so the acidified ethanol was neutralized. When an acid or neutral sorbent, the acidified ethanol is not neutralized.

What is claimed is:

1. A process for the analysis of gentain violet in a material which comprises:
   a. finely particulating a known amount of material containing gentian violet, unless such material is already in a finely divided state;
   b. admixing a known amount of acidified ethanol with said finely particulated material and letting the resultant admixture stand, said acidified ethanol removing said gentian violet from said material;
   c. separating said acidified ethanol (b) from said admixture (b) by centrifugation;
   d. removing any spectrophotometrical interfering substance from said acidified ethanol (c) by passing said acidified ethanol (c) through a chromatograph column, containing a basic sorbent, the acid in said acidified ethanol (c) being neutralized;
   e. concentrating said neutralized ethanol (d) so that the concentration of said gentian violet therein is increased;
   f. determining the amount of getian violet in said neutralized ethanol (e) and the background measurement of said neutralized ethanol (e) by spectrophotometrical means;
   g. quenching said gentian violet in said neutralized ethanol (e) by adding to said neutralized ethanol (e) a chemical substance which selectively renders said gentian violet non-detectable by spectrophotometric means without disturbing the spectrophotometric background of said neutralized ethanol;
   h. determining the background measurement of said neutralized ethanol (e) by spectrophotometrical means; and
   i. calculating the quantitative amount of gentian violet in said material using the spectrophotometrical measurements of steps (f) and (h).

2. A process as described in claim 1 wherein said material containing gentian violet is animal tissue, poultry tissue, eggs, animal feed, poultry feed, animal manure or poultry manure.

3. A process as described in claim 1 wherein said acidified ethanol was acidified by HCl.

4. A process as described in claim 1 wherein said basic sorbent is Alumin-AR.

5. A process as described in claim 1 wherein said neutralized ethanol (e) is concentrated in step (d) is concentrated by a factor of at least tenfold.

6. A process as described in claim 1 wherein said spectrophotometric measurements in steps (f) and (h) are made at 590 m$\mu$.

7. A process for checking the accuracy of a process for the analysis of gentian violet in a material which comprises:
   a. finely particulating a known amount of a material known not to contain any gentian violet, unless such material is already in a finely divided state;
   b. adding a known amount of at least one aqueous solution containing a known amount of gentian violet to a known amount of said material known not to contain any gentian violet to form at least one spiked sample;
   c. admixing a known amount of acidified ethanol with said spiked sample and letting the resultant admixture stand, said acidified ethanol removing said gentian violet from said material;
   d. separating said acidified ethanol (b) from said admixture (c) by centrifugation;
   e. removing any spectrophotometrical interfering substance from said acidified ethanol (d) by passing said acidified ethanol (d) through a chromatograph column containing a basic sorbent, the acid in said acidified ethanol (d) being neutralized;
   f. concentrating said neutralized ethanol (d) so that the concentration of said gentian violet therein is increased;
   g. determining the amount of gentian violet in said neutralized ethanol (f) and the background measurement of said neutralized ethanol (f) by spectrophotometrical means;
   h. quenching said gentian violet in said neutralized ethanol (f) by adding to said neutralized ethanol (f) a chemical substance which selectively renders said gentian violet non-detectable by spectrophotometric means without disturbing the spectrophotometric background of said acidified ethanol;
   i. determining the background measurement of said neutralized ethanol (f) by spectrophotometrical means; and
   j. calculating the quantitative amount of gentian violet in said spiked material using the spectrophotometrical measurements of steps (g) and (i), said amount (i) of gentian violet for said spiked sample giving the accuracy of the procedure for the analysis of gentian violet in said spiked material by direct comparison with the known amount of gentian violet placed in said spiked sample in step (b).

8. A process as described in claim 7 wherein at least two spiked samples are prepared in step (b), each of said spiked samples having a different amount of gentian violet.

9. A process as described in claim 7 wherein said material containing gentian violet is animal tissue, poultry tissue, eggs, animal feed, poultry feed, animal manure or poultry manure.

10. A process as described in claim 7 wherein said basic sorbent is Alumin-AR.

11. A process as described in claim 7 wherein said neutralized ethanol is concentrated by a factor of at least tenfold.

12. A process as described in claim 7 wherein said acidified ethanol was acidified by HCl.

13. A process as described in claim 7 wherein said spectrophotometric measurements in steps (e) and (g) are made at 590 m$\mu$.

14. A process for the analysis of gentian violet in a material which comprises:
 a. finely particulating a known amount of material containing gentian violet, unless such material is already in a finely divided state;
 b. admixing a known amount of acidified ethanol with said finely particulated material and letting the resultant admixture stand, said acidified ethanol removing said gentian violet from said material;
 c. separating said acidified ethanol (b) from said admixture (b) by centrifugation;
 d. removing any spectrophotometric interfering substance from said acidified ethanol (c) by passing said acidified ethanol (c) through a chromatograph column, containing a basic sorbent, the acid in said acidified ethanol (c) being neutralized;
 e. determining the amount of gentian violet in said neutralized ethanol (d) and the background measurement of said neutralized ethanol (d) by spectrophotometrical means;
 f. quenching said gentian violet in said neutralized ethanol (d) by adding to said neutralized ethanol (d) a chemical substance which selectively renders said gentian violet non-detectable by spectrophotometric means without disturbing the spectrophotometric background of said neutralized ethanol;
 g. determining the background measurement of said neutralized ethanol (d) by spectrophotometrical means; and
 h. calculating the quantitative amount of gentian violet in said material using the spectrophotometrical measurements of steps (e) and (g).

15. A process as described in claim 14 wherein said material containing gentian violet is animal tissue, poultry tissue, eggs, animal feed, poultry feed, animal manure or poultry manure.

16. A process as described in claim 14 wherein said acidified ethanol was acidified by HCl.

17. A process as described in claim 14 wherein said basic sorbent is Alumin-AR.

18. A process as described in claim 14 wherein said spectrophotometric measurements in steps (e) and (g) are made at 590 m$\mu$.

19. A process for checking the accuracy of a process for the analysis of gentian violet in a material which comprises;
 a. finely particulating a known amount of a material known not to contain any gentain violet, unless such material is already in a finely divided state;
 b. adding a known amount of at least one aqueous solution containing a known amount of gentian violet to a known amount of said material known not to contain any gentain violet to form at least one spiked sample;
 c. admixing a known amount of acidified ethanol with said spiked sample and letting the resultant admixture stand, said acidified ethanol removing said gential violet from said material;
 d. separating said acidified ethanol (b) from said admixture (c) by centrifugation;
 e. removing any spectrophotometrical interfering substance from said acidified ethanol (d) by passing said acidified ethanol (d) through a chromatograph column containing a basic sorbent, the acid in said acidified ethanol (d) being neutralized;
 f. determining the amount of gentian violet in said neutralized ethanol (e) and the background measurement of said neutralized ethanol (e) by spectrophotometrical means;
 g. quenching said gentain violet in said neutralized ethanol (e) by adding to said neutralized ethanol (e) a chemical substance which selectively renders said gentian violet non-detectable by spectrophotomertic means without disturbing the spectrophotometric background of said acidified ethanol;
 h. determining the background measurement of said neutralized ethanol (e) by spectrophometrical means; and
 i. calculating the quantitative amount of gentian violet in said spiked material using the spectrophotometrical measurements of steps (f) and (h), said amount (h) of gentian violet for said spiked sample giving the accuracy of the procedure for the analysis of gentian violet in spiked material by direct comparison with the known amount of gentian violet placed in said spiked sample in step (b).

20. A process as described in claim 19 wherein at least two spiked samples are prepared in step (b), each of said spiked samples having a different amount of gentian violet.

21. A process as described in claim 19 wherein said material containing gentian violet is animal tissue, poultry tissue, eggs, animal feed, poultry feed, animal manure or poultry manure.

22. A process as described in claim 19 wherein said basic sorbent in Alumin-AR.

23. A process as described in claim 19 wherein said acidified ethanol was acidified by HCl.

24. A process as described in claim 19 wherein said spectrophotometric measurements in steps (e) and (f) are made at 590 m$\mu$.

* * * * *